(12) United States Patent
Yang et al.

(10) Patent No.: US 9,595,428 B2
(45) Date of Patent: Mar. 14, 2017

(54) CELLULAR PROBE DEVICE, SYSTEM AND ANALYSIS METHOD

(71) Applicant: The Board of Regents of The University of Oklahoma, Norman, OK (US)

(72) Inventors: Zhibo Yang, Norman, OK (US); Qiang Liu, Edmond, OK (US); Ning Pan, Norman, OK (US)

(73) Assignee: The Board of Regents of the University Oklahoma, Norman, OK (US)

( * ) Notice: Subject to any disclaimer, the term of this patent is extended or adjusted under 35 U.S.C. 154(b) by 0 days.

(21) Appl. No.: 14/742,485

(22) Filed: Jun. 17, 2015

(65) Prior Publication Data

US 2015/0364306 A1 Dec. 17, 2015

Related U.S. Application Data

(60) Provisional application No. 62/013,360, filed on Jun. 17, 2014.

(51) Int. Cl.
| | |
|---|---|
| *H01J 49/26* | (2006.01) |
| *H01J 49/04* | (2006.01) |
| *G01N 1/02* | (2006.01) |
| *H01J 49/00* | (2006.01) |

(52) U.S. Cl.
CPC ............ *H01J 49/0404* (2013.01); *G01N 1/02* (2013.01); *H01J 49/0459* (2013.01); *G01N 2001/028* (2013.01); *H01J 49/0004* (2013.01)

(58) Field of Classification Search
USPC ......................................... 250/281, 282, 288
See application file for complete search history.

(56) References Cited

U.S. PATENT DOCUMENTS

| | | | |
|---|---|---|---|
| 5,245,185 | A | 9/1993 | Busch et al. |
| 6,478,238 | B1 | 11/2002 | Wachs et al. |
| 6,803,566 | B2 | 10/2004 | Van Berkel |
| 7,105,812 | B2 | 9/2006 | Zhao et al. |

(Continued)

FOREIGN PATENT DOCUMENTS

WO 01/94931 12/2001

OTHER PUBLICATIONS

Modestov, et al.; "Scanning Capillary Microscopy/Mass Spectrometry for Mapping Spatial Electrochemical Activity of Electrodes"; Analytical Chemistry; vol. 73, No. 17, Sep. 1, 2001; pp. 4229-4240.

(Continued)

*Primary Examiner* — Nicole Ippolito
(74) *Attorney, Agent, or Firm* — Hall Estill Law Firm

(57) ABSTRACT

A sampling probe, system and analysis method is disclosed. The sampling probe includes a tube having at least a first bore, a second bore, a first end, and a tapered second end; a first capillary partially disposed within the first bore, at least a portion of the first capillary extending from the first end of the tube; a second capillary partially disposed within the second bore, the second capillary having a portion with a free tapered end which extends from the first end of the tube; and wherein an end of the first capillary and an end of the second capillary converge at a junction in the tapered second end of the tube.

11 Claims, 13 Drawing Sheets

(56) References Cited

U.S. PATENT DOCUMENTS

| | | | |
|---|---|---|---|
| 8,110,797 | B2 | 2/2012 | Marshall et al. |
| 8,530,834 | B2 | 9/2013 | Marshall et al. |
| 2006/0273808 | A1 | 12/2006 | Van Berkel et al. |
| 2012/0153143 | A1 | 6/2012 | Kennedy et al. |
| 2014/0014747 | A1* | 1/2014 | Moeller .................. H01J 49/10 239/690 |
| 2015/0158051 | A1* | 6/2015 | Hoerr ...................... A61L 27/34 427/2.1 |

OTHER PUBLICATIONS

Wachs, et al.; "Electrospray Device for Coupling Microscale Separations and Other Miniaturized Devices with Electrospray Mass Spectrometry"; Analytical Chemistry; vol. 73, No. 3, Feb. 1, 2001; pp. 632-638.

Van Berkel; "Thin-Layer Chromatography and Electrospray Mass Spectrometry Coupled Using a Surface Sampling Probe"; Analytical Chemistry; vol. 74, No. 24, Dec. 12, 2002; pp. 6216-6223.

Gun, et al.; "Studies on the Reduction of $[(C_5Me_5)_2Mo_2O_5]$ in Methanol/Water/Acetate Solutions by On-Line Electrochemical Flowcell and Electrospray Mass Spectrometry"; Eur. J. Inorg. Chem.; 2003; pp. 482-492.

Gun, et al.; "Reduction of $[(C_5Me_5)_2Mo_2O_5]$ and $[(C_5Me_5)_2Mo_2O_4]$ in Methanol/Water/Trifluoroacetate Solutions Investigated by Combined On-Line Electrochemistry/Electrospray-Ionization Mass Spectrometry"; Eur. J. Inorg. Chem.; 2003; pp. 2264-2272.

Wachs, et al., "A Device for Automated Direct Sampling and Quantitation from Solid-Phase Sorbent Extraction Cards by Electrospray Tandem Mass Spectrometry"; Analytical Chemistry; vol. 75, No. 7, Apr. 1, 2003; pp. 1769-1775.

Ford, et al.; "An improved thin-layer chromatography/mass spectrometry coupling using a surface sampling probe electrospray ion trap system"; Rapid Communications in Mass Spectrometry; vol. 18; 2004; pp. 1303-1309.

Modestov, et al.; "Radial Electrochemical Flow Cell for On-Line Coupling with Mass Spectrometry: Theory and Electrooxidation of Dimethylaminomethyl Ferrocene"; Electroanalysis; vol. 16, No. 5; 2004; pp. 367-378.

Modestov, et al.; "On-line electrochemical-mass spectrometry study of the mechanism of oxidation of N,N-dimethyl-p-phenylenediamine in aqueous electrolytes"; Journal of Electroanalytical Chemistry; vol. 565; 2004; pp. 7-19.

Asano, et al.; "Self-aspirating atmospheric pressure chemical ionization source for direct sampling of analytes on surfaces and in liquid solutions"; Rapid Communications in Mass Spectrometry; vol. 19; 2005; pp. 2305-2312.

Ford, et al.; "Thin-layer chromatography/electrospray ionization triple-quadrupole linear trap mass spectrometry system: analysis of rhodamine dyes separated on reversed-phase C8 plates"; Journal of Mass Spectrometry; vol. 40; 2005; pp. 866-875.

Ford, et al.; "Quantitative Thin-Layer Chromatography/Mass Spectrometry Analysis of Caffeine Using a Surface Sampling Probe Electrospray Ionization Tandem Mass Spectrometry System"; Analytical Chemistry; vol. 77, No. 14; Jul. 15, 2005; pp. 4385-4389.

Kertesz, et al.; "Automation of a Surface Sampling Probe/Electrospray Mass Spectrometry System"; Analytical Chemistry; vol. 77, No. 22; Nov. 15, 2005; pp. 7183-7189.

Kelly, et al.; "Chemically Etched Open Tubular and Monolithic Emitters for Nanoelectrospray Ionization Mass Spectrometry"; Analytical Chemistry; vol. 78, No. 22; Nov. 15, 2006; pp. 7796-7801.

Van Berkel, et al.; "Evaluation of a surface-sampling probe electrospray mass spectrometry system for the analysis of surface-deposited and affinity-captured proteins"; Rapid Communications in Mass Spectrometry; vol. 20; 2006; pp. 1144-1152.

Roach, et al.; "Nonspray desorption electrospray ionization: an ambient method for liquid-extraction surface sampling in mass spectrometry"; Analyst, The Royal Society of Chemistry; vol. 135; 2010; pp. 2233-2236.

Laskin, et al.; "Tissue Imaging Using Nanospray Desorption Electrospray Ionization Mass Spectrometry"; Analytical Chemistry; vol. 84, No. 1; 2012; pp. 141-148.

Tsuyama, et al.; "Molecular and Functional Analysis of Cellular Phenomena Using Single-Cell Mass Spectrometry"; Biol. Pharm. Bull.; vol. 35, No. 9; 2012; pp. 1425-1431.

Lanekoff, et al.; "Spatially resolved analysis of glycolipids and metabolites in living *Synechococcus* sp. PCC 7002 using nanospray desorption electrospray ionization"; Analyst, The Royal Society of Chemistry; vol. 138; 2013; pp. 1971-1978.

Bonislawski, Adam; "University of Oklahoma Team Develops Device for Mass Spec Analysis of Living Single Cells"; ProteoMonitor / GenomeWeb; Oct. 10, 2014; 4 pages.

Pan, Ning, et al.; "The Single-Probe: A Minitiarized Multifunctional Device for Single Cell Mass Spectrometry Analysis"; Analytical Chemistry; Published: Sep. 15, 2014; vol. 86; pp. 9376-9380.

Pan, Ning, et al.; "Single-probe Mass Spectrometry for Single Cell Analysis : Development and Applications"; Department of Chemistry and Biochemistry; University of Oklahoma; Conference on Ion Chemistry and Mass Spectrometry; Jan. 18, 2014; 16 pages.

Pan, Ning, et al.; Single-probe Mass Spectrometry: a Novel Method for Single Cell Analysis; Department of Chemistry and Biochemistry; University of Oklahoma; American Society for Mass Spectrometry; Sep. 18, 2014; 16 pages.

Pan, Ning, et al.; "Single-Probe: A Novel Sampling and Ionization Device for Mass Spectrometry Studies of Single Cells, Biological Tissues, and Sulfated Biomolecules"; Department of Chemistry and Biochemistry; University of Oklahoma; American Society for Mass Spectrometry; Sep. 18, 2014; 1 page.

Rao, Wei, et al.; "High resolution ambient MS imaging of mouse tissue by surface micro-extraction using the Single-probe"; Department of Chemistry and Biochemistry; University of Oklahoma; American Society for Mass Spectrometry; Sep. 18, 2014; 1 page.

Vowcicefski, Rachel, et al.; "Novel Ionization Method of Sulfated Peptides Using the Single-Probe Ionization Source"; Department of Chemistry and Biochemistry; University of Oklahoma; American Society for Mass Spectrometry; Sep. 18, 2014; 1 page.

\* cited by examiner

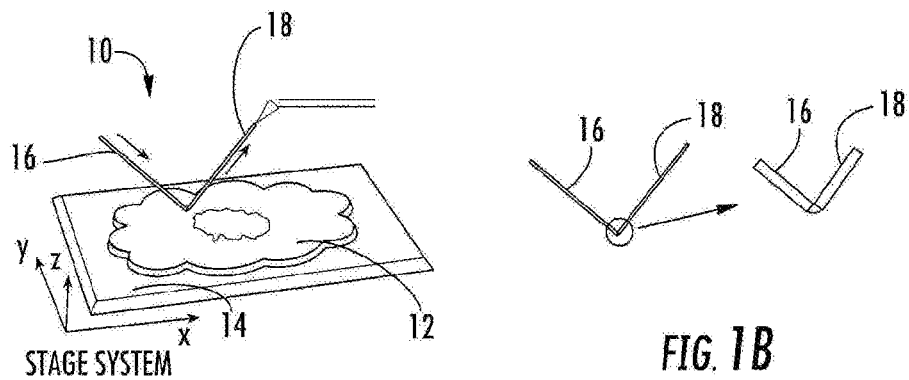
FIG. 1A
FIG. 1B
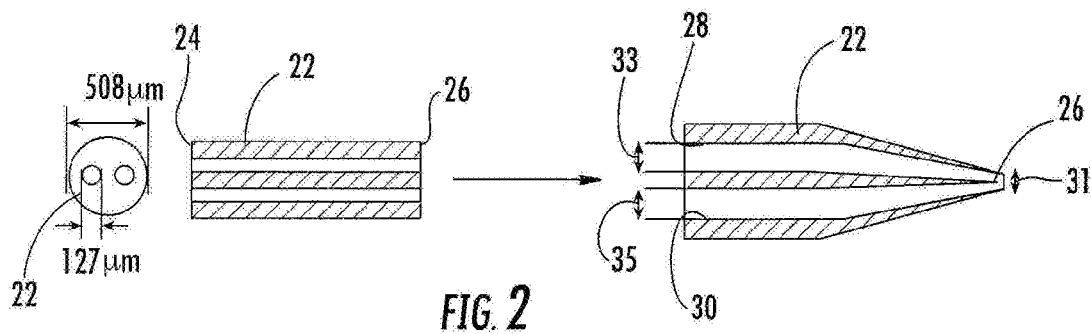
FIG. 2
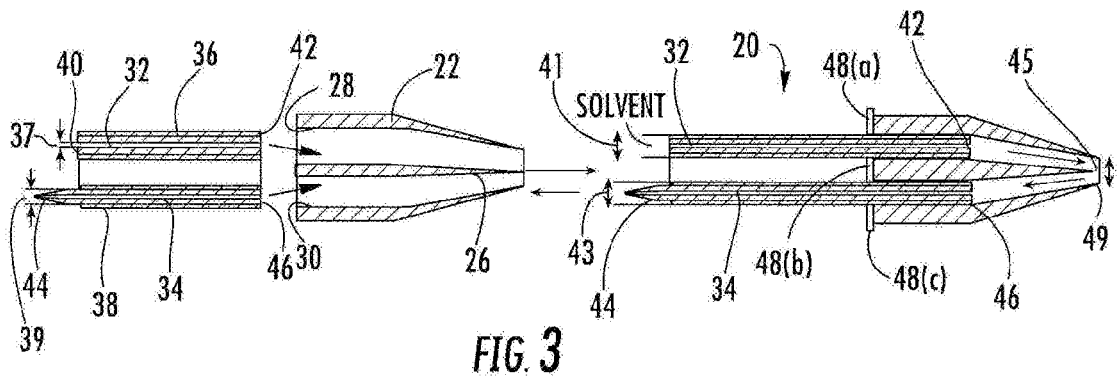
FIG. 3

CELLULAR PROBE DEVICE, SYSTEM AND ANALYSIS METHOD

CROSS REFERENCE TO RELATED APPLICATIONS/INCORPORATION BY REFERENCE STATEMENT

The present patent application claims priority to the United States Provisional Patent Application identified by U.S. Ser. No. 62/013,360 which was filed on Jun. 17, 2014, entitled "CELLULAR PROBE DEVICE, SYSTEM AND ANALYSIS METHOD," the entire contents of which are hereby incorporated herein by reference.

STATEMENT REGARDING FEDERALLY SPONSORED RESEARCH OR DEVELOPMENT

Not applicable.

BACKGROUND

Mass spectrometry imaging (MSI) is an emerging tool for mapping the spatial distribution of analytes in biological tissues at the molecular level. MSI has been successfully utilized to obtain rapid 2-D or 3-D spatial distributions of biological species (e.g., lipids, drugs and metabolites) present on different tissue slices (e.g., kidney, brain, liver, and tumor). This emerging scientific technology has the potential to reshape the analytical science of many research disciplines including human medicine, e.g., drug delivery and metabolomics, target cancer therapy, and cancer diagnosis.

A pivotal focus of MSI technique development is the improvement of the spatial resolution, and an ultimate goal in detection resolution is the ability to sample a single cell with mass spectrometry (MS). The ability to interrogate the molecular constituents of individual cells will be a major advancement in biological science. Currently and classically, molecular cell component analysis is almost exclusively done through lysate preparation of a cell population or a tissue sample, and all analysis represents an average of the disparate characteristics of the individual cells present; this limitation applies to common experimental analysis methods such as Western blotting and lipid analysis. Additionally, the preparation of a lysate or an extract from such a heterogeneous sample creates a completely ex vivo biological context—extremely disruptive reagents or processes rip apart the rigorous-spatially segregated cell, mixing all the constituents into a completely artificial milieu. This less-than-ideal experimental approach has been necessary due to the lack of analytical sampling sensitivity, and it is currently impossible to know how this deficient sample preparation system might have produced incorrect or biased results in countless experiments over the modern history of biological science. Single cell MS has the potential to completely change the paradigm of biological sampling for molecular analysis, and the impact of this technical advancement is impossible to underestimate.

Depending on the ionization environment, MSI can be generally classified into two major categories: (a) MSI under vacuum, such as secondary ion mass spectrometry (SIMS) and matrix-assisted laser desorption ionization (MALDI), and (b) ambient pressure MSI, such as desorption electrospray ionization (DESI), laser ablation electrospray ionization mass spectrometry (LAESI), and nanospray desorption electrospray ionization (nano-DESI). Although all above techniques, except for nano-DESI, have been commercialized, their applications are still limited by their drawbacks. Due to the difficulties to obtained high vacuum for samples containing water, the application of SIMS to biological systems has been greatly limited. In spite that MALDI has become the major technique for MIS, surface treatment is obligatory and very time-consuming. In addition, there are concerns regarding the influence of sample preparation on the spatial distribution of analytes. The development of ambient desorption/ionization techniques allows rapid imaging measurement without (or very little, if any) treatment of surfaces. However, these MSI techniques, including DESI, LAESI, and nano-DESI, have their own inherent shortcomings. For example, DESI has relatively low spatial resolution as well as issues of sensitivity, ionization efficiency, and tissue-specific ion suppression effects. LAESI is a destructive method, such that experiments are nearly non-reproducible. Nano-DESI is non-destructive and provides a high resolution, whereas the fabrication of the imaging probes and the operation of the device are challenging. Therefore, the development of new methods to improve existing MSI technique is urgently needed.

BRIEF DESCRIPTION OF THE DRAWINGS

Several embodiments of the presently disclosed inventive concepts are hereby illustrated in the appended drawings. It is to be noted however, that the appended drawings only illustrate several typical embodiments and are therefore not intended to be considered limiting of the scope of the presently disclosed inventive concepts. Further, in the appended drawings, like or identical reference numerals or letters may be used to identify common or similar elements and not all such elements may be so numbered. The figures are not necessarily to scale and certain features and certain views of the figures may be shown as exaggerated in scale or in schematic in the interest of clarity and conciseness. The bore dimensions shown in the figures are not limited to those shown therein and are only intended to be exemplary.

FIG. 1(a) depicts a conventional nano-DESI dual capillary imaging probing system and its use with a mass spectrometer to sample a tissue on an X-Y-Z movable stage system.

FIG. 1(b) is a close-up view of two capillaries of the system of FIG. 1.

FIG. 2 depicts in a sectional view one non-limiting embodiment of how a dual-bore tube can be pulled to form a narrow tip in one end.

FIG. 3 depicts in a sectional view how coated capillaries are inserted into a pulled dual-bore tube of FIG. 2 in accordance with one non-limiting embodiment of the present disclosure.

DETAILED DESCRIPTION

Figure 4:
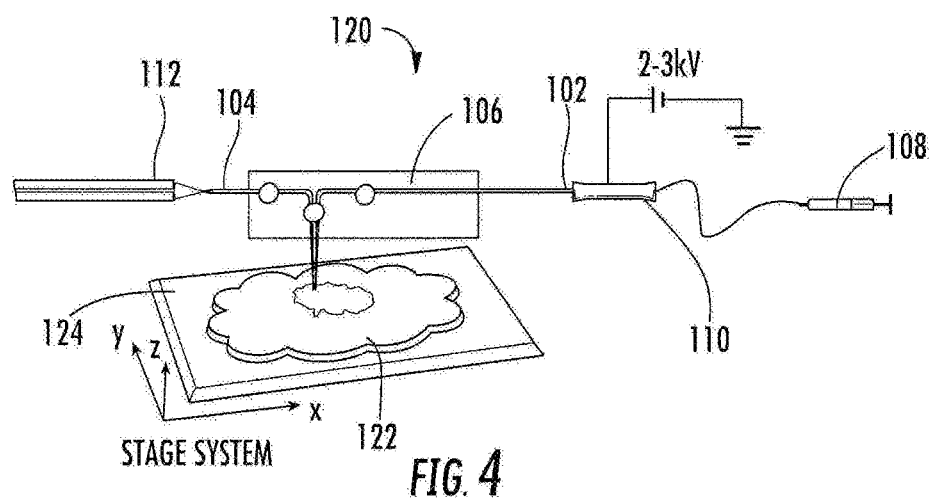
FIG. 4 depicts an experimental set up of a Single-probe MSI system of the present disclosure including a Single-probe, and a MS, and a solvent supplying device.

Before describing various embodiments of the presently disclosed inventive concepts in more detail by way of exemplary description, examples, and results, it is to be understood that the presently disclosed inventive concepts are not limited in application to the details of methods and compositions as set forth in the following description. The presently disclosed inventive concepts are capable of other embodiments or of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the presently disclosed inventive concepts may be practiced without these specific details. In other instances, features which are well known to persons of ordinary skill in the art have not been described in detail to avoid unnecessary complication of the description.

Unless otherwise defined herein, scientific and technical terms used in connection with the presently disclosed inventive concepts shall have the meanings that are commonly understood by those having ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which the presently disclosed inventive concepts pertain. All patents, published patent applications, and non-patent publications referenced in any portion of this application are herein expressly incorporated by reference in their entirety to the same extent as if each individual patent or publication was specifically and individually indicated to be incorporated by reference.

All of the compositions and methods of production and application thereof disclosed herein can be made and executed without undue experimentation in light of the present disclosure. While the compositions and methods of the presently disclosed inventive concept have been described in terms of particular embodiments, it will be apparent to those of skill in the art that variations may be applied to the compositions and/or methods and in the steps or in the sequence of steps of the method described herein without departing from the concept, spirit and scope of the inventive concepts. All such similar substitutes and modifications apparent to those of skill in the art are deemed to be within the spirit, scope and concept of the inventive concepts as defined herein.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the study subjects. Further, in this detailed description and the appended claims, each numerical value (e.g., temperature or time) should be read once as modified by the term "about" (unless already expressly so modified), and then read again as not so modified unless otherwise indicated in context. Also, any range listed or described herein is intended to include, implicitly or explicitly, any number within the range, particularly all integers, including the end points, and is to be considered as having been so stated. For example, "a range from 1 to 10" is to be read as indicating each possible number, particularly integers, along the continuum between about 1 and about 10. Thus, even if specific data points within the range, or even no data points within the range, are explicitly identified or specifically referred to, it is to be understood that any data points within the range are to be considered to have been specified, and that the inventors possessed knowledge of the entire range and the points within the range.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

Where used herein the term "conductive material" includes any electrically-conductive material such as a metal, including but not limited to: gold, platinum, titanium; an inorganic, including but not limited to: diamond-like carbon and silicon monoxide; and a conductive polymer, including but not limited to polyaniline and a polypropylene/graphite mixture).

In at least one embodiment the presently disclosed inventive concepts are directed to a new nano-DESI probe in which two fused capillaries (e.g., silica capillaries having outer diameter (OD)=150 µm and inner diameter (ID)=50 µm ID) are combined in a single unit to fabricate one sampling probe, the probe having a junction at the fused tips of the two capillaries. During a sampling measurement, a solvent (e.g., a methanol/water solution) is supplied through one capillary. The solvent dissolves the analytes on a small spot of the sample surface at the junction of the tips of the two capillaries. The solution containing the dissolved analytes is then collected at the tip of the second capillary and is transported through the second capillary to a narrowed orifice at an emitter end where the solution is ionized into charged droplets at an inlet of a mass spectrometer in a similar way of a conventional nano-spray ionization source. The ionized species in the solution are then analyzed the mass spectrometer, and m/z (mass/charge) information is collected and saved, e.g., by a computer. The sample slice can be placed on a motorized stage system, in which three stages can be independently controlled through a computer program, whereby the location information of analytes on the target spot can be recorded simultaneously along with their ion intensities. Eventually, the spatial distribution of molecules of interest can be mapped using visualization software by integrating information of both ion signal intensities and the corresponding coordinates.

Referring to FIGS. 1(a) and 1(b), a conventional nano-DESI dual capillary imaging probing system 10 is shown in use with a mass spectrometer (not shown) to sample a tissue 12 on an X-Y-Z movable system 14. A first capillary 16 for providing a charged solvent to the tissue and a second capillary 18 for receiving the analyte sampled by the mass spectrometer are utilized in the system 10. In conventional nano-DESI probe techniques (e.g., shown in FIG. 1) because two independent capillaries are needed to assemble the probe, systematic tests must be carried out to identify optimum parameters to determine the arrangement of the two capillaries, including the contact angle and distance, relative height, and profile of capillary orifice. Although adequate experience can be built up during the practice, it is still difficult to have a good quality control when fabricating a batch of such probes for series experiments. Due to these inherent drawbacks, fabricating prior nano-DESI probes has been very labor intensive and requires significant amount of experience. As a result this technique has not been widely adopted.

In the presently disclosed novel Single-probe the two capillaries have been integrated into an integral unit (the Single-probe) which can be directly coupled with a movable stage system and a MS for analysis of tissues and cells.

In certain embodiments, the Single-probe MSI of the presently disclosed inventive concepts can be used to investigate the distribution of anti-cancer drugs (e.g., deguelin) in a variety of tissues (such as but not limited to, liver, kidney, brains, and breast cancer tumors) whereby 3-D images can be obtained by extrapolating 2-D images of a series of sections of an organ or a tumor.

EXAMPLES

The presently disclosed inventive concepts, having now been generally described, will be more readily understood by reference to the following examples and embodiments, which are included merely for purposes of illustration of certain aspects and embodiments of the presently disclosed inventive concepts, and are not intended to be limiting. The following detailed examples of methods of use and construction of the presently disclosed inventive concepts and are to be construed, as noted above, only as illustrative, and not as limitations of the disclosure in any way whatsoever. Those skilled in the art will promptly recognize appropriate variations from the various structure, components, procedures and methods.

Example 1

As noted above, in at least one embodiment, the Single-probe device is constructed by incorporating at least two separate capillaries into a single integrated unit. Referring to FIG. 2-3, one non-limiting example of how a Single-probe 20 is constructed is described below: (1) Provide a dual-bore glass tube 22 having a first end 24 and a second end 26 (e.g., 508 µm OD, 127 µm ID, Friedrich & Dimmock, Inc.). Cut the dual-bore glass tube into ~5 cm long pieces, and pull a sharp tip on the second end 26 using a puller (not shown) (e.g., KOPF Vertical Pipette Puller, P-720) on the second end 26 (FIG. 2) so that the tube 22 is provided with a first bore 28 and a second bore 30. The tapered second end 26 of the tube 22 has an outer diameter 31 in a range of 0.1 µm to 50 µm. The first bore 28 and second bore 30 of the tube 22 have inner diameters 33 and 35 in a range of 1 µm to 500 µm.

(2) Provide a pair of fused silica capillary tubes 32 and 34 having outer polyimide coating material 36 and 38 (e.g., 150 µm OD, 50 µm ID, 5 cm long, PolyMicro Technologies). The tube 32 having a first end 40 and a second end 42. The tube 34 having a first end 44 and a second end 46. Remove the outer polyimide coating material 38 from an end 44 of one fused silica capillary 34 and pull the decoated end 44 into a sharp tip so that the decoated end 44 is sharp and narrowed and the other end 46 is blunt (FIG. 3). The first capillary 32 and second capillary 34 of the sampling probe 20 have inner diameters 37 and 39, respectively, in a range of 1 µm to 150 µm and outer diameters 41 and 43, respectively, in a range of 5 µm to 450 µm.

(3) Insert blunt ends 42 and 46 of the two capillaries 32 and 34 into the bores 28 and 30 of the pulled glass tubing 22 obtained from step 1, seal gaps 48(a)-48(c) using UV-light active epoxy (e.g., Prime Dent Light Cure Resin Dental Bonding Adhesive), and irradiate the entire piece with UV light for 30 seconds to form the integrated Single-probe 20 having a tip 49 (FIG. 3).

(4) The Single-probe 20 can then be used in conjunction with an MS apparatus as described in further detail below.

Example 2

As noted above, in at least one embodiment, the Single-probe device 20 is constructed by incorporating at least two separate capillaries into a single integrated unit. Another non-limiting example of how a Single-probe 50 is constructed is described below. Thus, the Single-probe 50 is constructed similar to the Single-probe 20 except as described herein:

(1) Provide a dual-bore glass tube 22 (e.g., 508 µm OD, 127 µm ID, Friedrich & Dimmock, Inc.). Cut the dual-bore glass tube 22 into ~5 cm long pieces, and pull a sharp tip using a puller (e.g., KOPF Vertical Pipette Puller, P-720) on one end 26 (as shown in FIG. 2).

Figure 5:
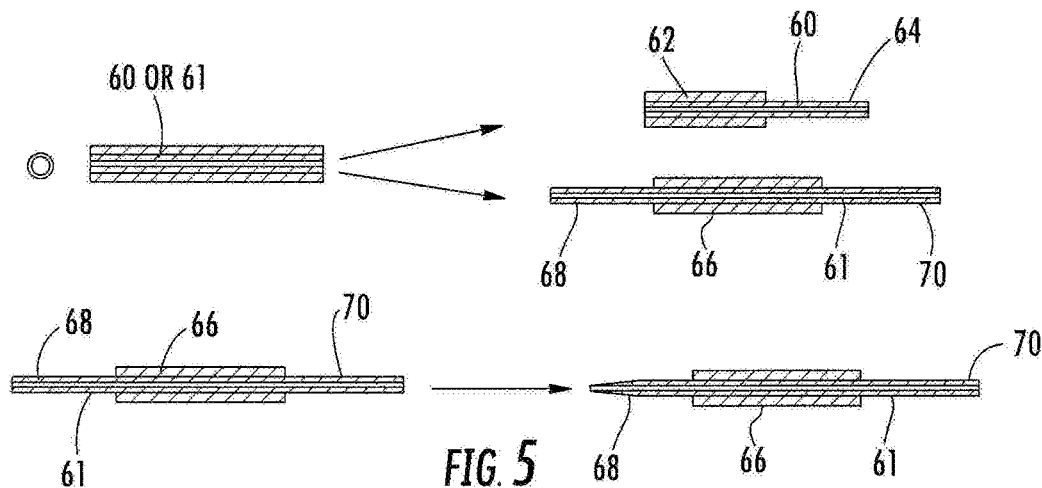
FIG. 5 depicts a non-limiting embodiment of how capillaries can be prepared for insertion by removal of a portion of the outer coating thereon.

(2) Referring to FIG. 5, provide a pair of fused silica capillary tubes 60 and 61 (e.g., 150 µm OD, 50 µm ID, 5 cm long, PolyMicro Technologies). Remove the outer coating material 62 from a portion of one end 64 of the first of the fused silica capillaries 60. Remove the outer coating material 66 from both ends 68 and 70 of the second fused silica capillary 61 (same type), and pull one end 68 of the second capillary 61 into a sharp tip (FIG. 5) so that one end 68 is sharp and narrowed and the other end 70 is blunt.

Figure 6:
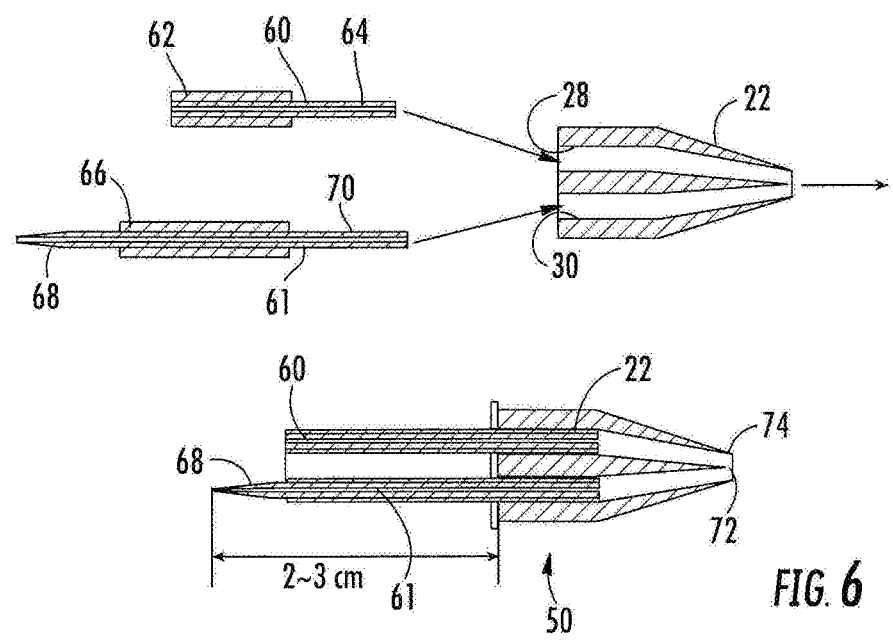
FIG. 6 depicts in a sectional view how the capillaries prepared in FIG. 5 are inserted into a pulled dual bore tube of FIG. 2 to form a Single-probe in accordance with one non-limiting embodiment of the present disclosure.

(3) Insert the exposed (decoated) blunt ends 64 and 70 of the two capillaries 60 and 61 into the bores 28 and 30 of the pulled glass tubing 22 obtained from step 1 (FIG. 2), seal gaps using UV-light active epoxy (e.g., Prime Dent Light Cure Resin Dental Bonding Adhesive), and irradiate the entire piece with UV light for 30 seconds to form the integrated Single-probe 50 (FIG. 6).

The Single-probe(s) 20 and 50 produced from Step 3 of either of Examples 1 or 2 may have slight deadspace 45 and 72 near the probe tip(s) 49 and 74, respectively. The solution containing analytes could be retained inside of the deadspace for a few more seconds (or fractions of seconds) before it is flushed by new solution which could slow down the detection speed. So, to solve this shortcoming, an alternative method is designed to fabricate a Single-probe 80 shown in Example 3.

Example 3

Figure 7:
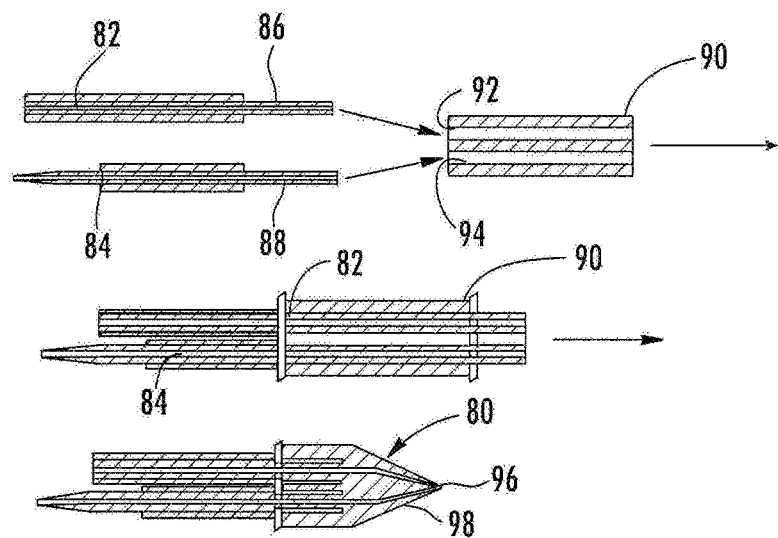
FIG. 7 depicts in a sectional view an alternate non-limiting embodiment of the present disclosure wherein a pair of capillaries as prepared in FIG. 3 can be inserted into a dual bore tube which is then pulled to form a narrow tip to form a Single-probe having a reduced deadspace in the junction tip.

Instead of pulling the fused silica capillaries and dual-bore glass tubing separately, as discussed above, insert decoated or uncoated blunt ends 86 and 88 of two fused silica capillaries 82 and 84, respectively, into a quartz dual-bore tube 90 having a first bore 92 and a second bore 94, glue both ends 86 and 88, and pull capillaries 82 and 84 and tube 90 all together using a laser puller (not shown) (e.g., such Sutter P-2000). The capillaries 82 and 84 and tube 90 melt simultaneously by leaser heating, and a similar Single-probe 80 with smaller deadspace 98 at the tip 96 is produced (FIG. 7).

Example 4

Figure 8:
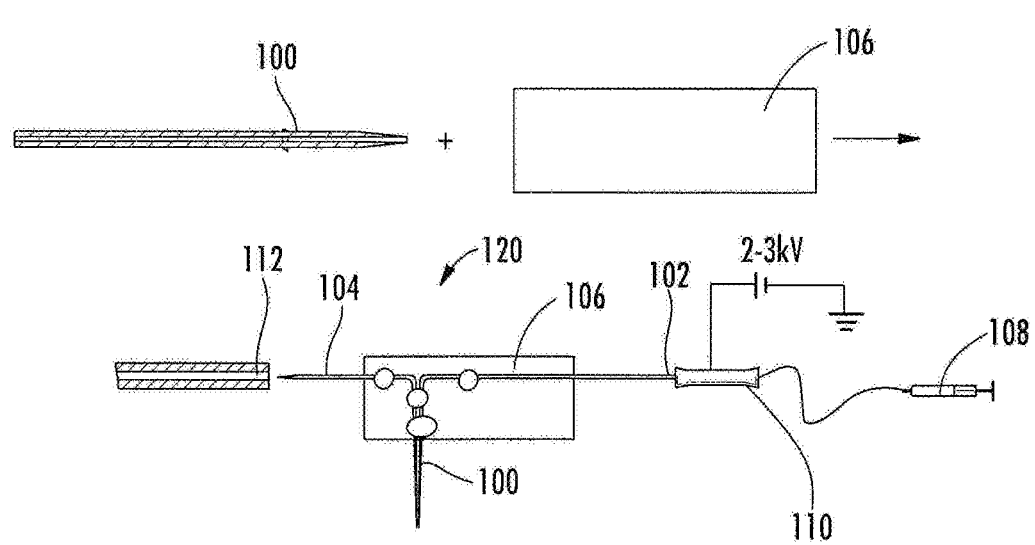
FIG. 8 depicts an experimental set up of a Single-probe MSI system of the present disclosure including a Single-probe on a support device which is attached via a micro-tight conductive union to a solvent supplying device.

The probe(s) from Examples 1-3, shown in FIGS. 4 and 8 as 100, or any other novel probe embodiment described herein can then be utilized with a MS apparatus to provide a Single-probe MSI system 120. For example, the probe 100 having a first end 102 and a second end 104 can be attached to a support 106 (e.g., a glass slide) for example using epoxy or glue. Connect the first end 102, which has a flat orifice, to a syringe 108 using a connector 110 such as a MicroTight Conductive Union (Upchurch Scientific); the voltage can be applied to the union. Attach the other end 104, which has a sharp emitter tip, to an inlet 112 of the mass spectrometer (not shown) (e.g., Thermo LTQ Orbitrap XL mass spectrometer). The system is ready for imaging measurement (FIG. 8). The Single-probe MSI system 120 can be used to measure a tissue 122 on an X-Y-Z movable system 124. In addition, the sharp tip can be inserted into a single cell, such that can directly detect the chemicals inside of cells. This feature of the Single-probe has not been obtained by using other current existing MSI techniques.

Example 5

Single Cell Mass Spectrometry

Figure 9:
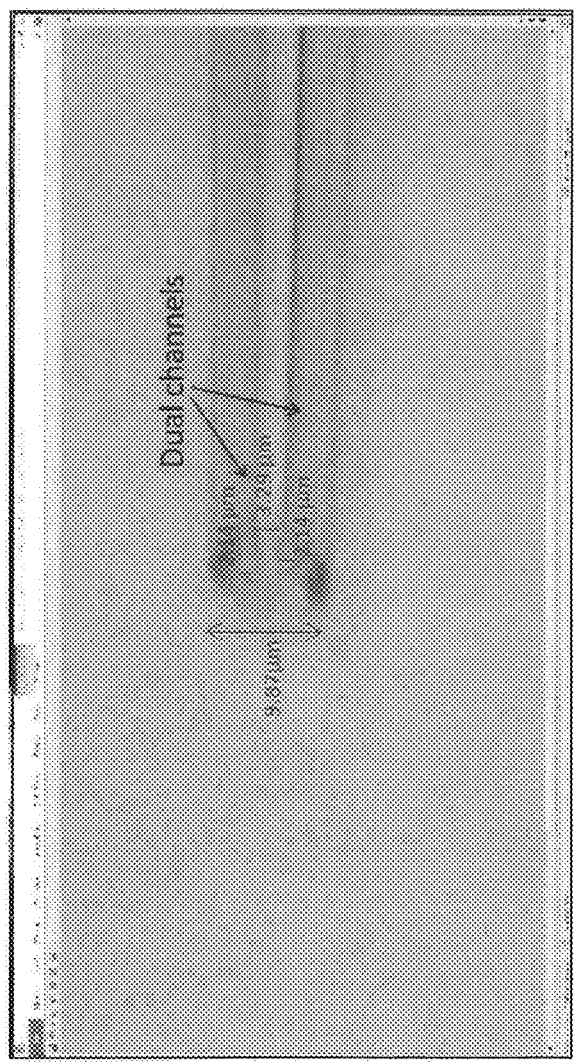
FIG. 9 is a photograph of a tip of the Single-probe in one non-limiting embodiment of the present disclosure. The bore dimensions of the probe, obtained using a digital microscope, are not limited to those shown in the photograph.
Figure 10:
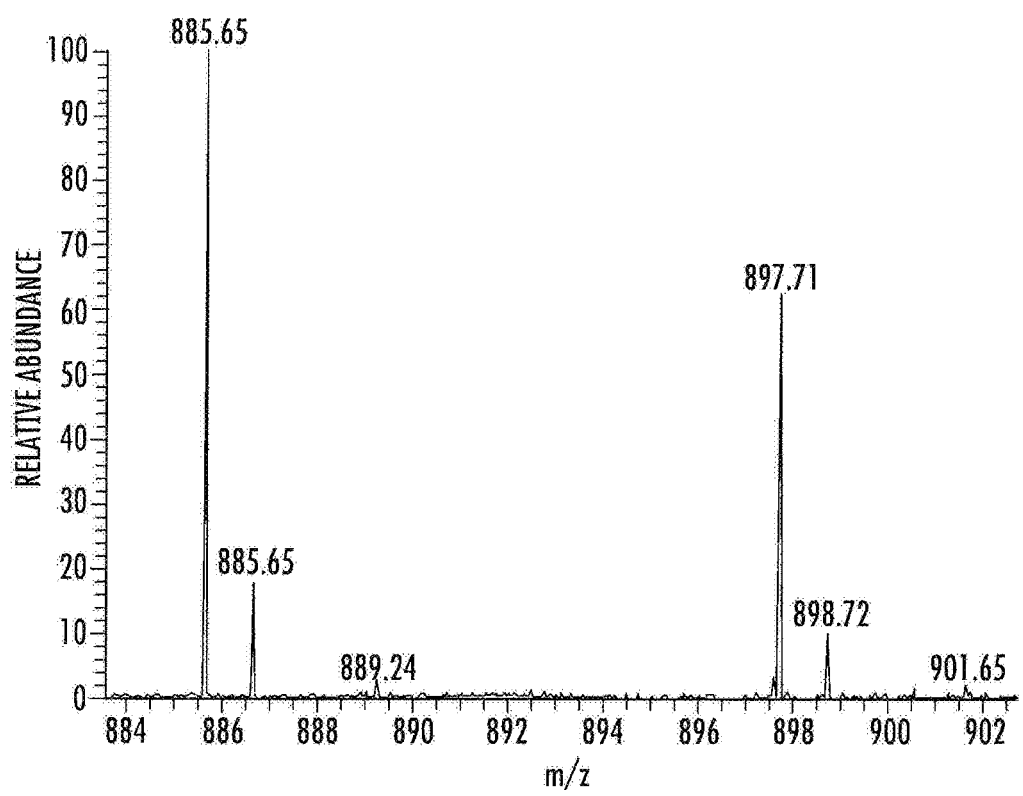
FIG. 10 depicts mass spectra obtained using a Single-probe inserted into a phosphate buffered saline (control) solution.
Figure 11:
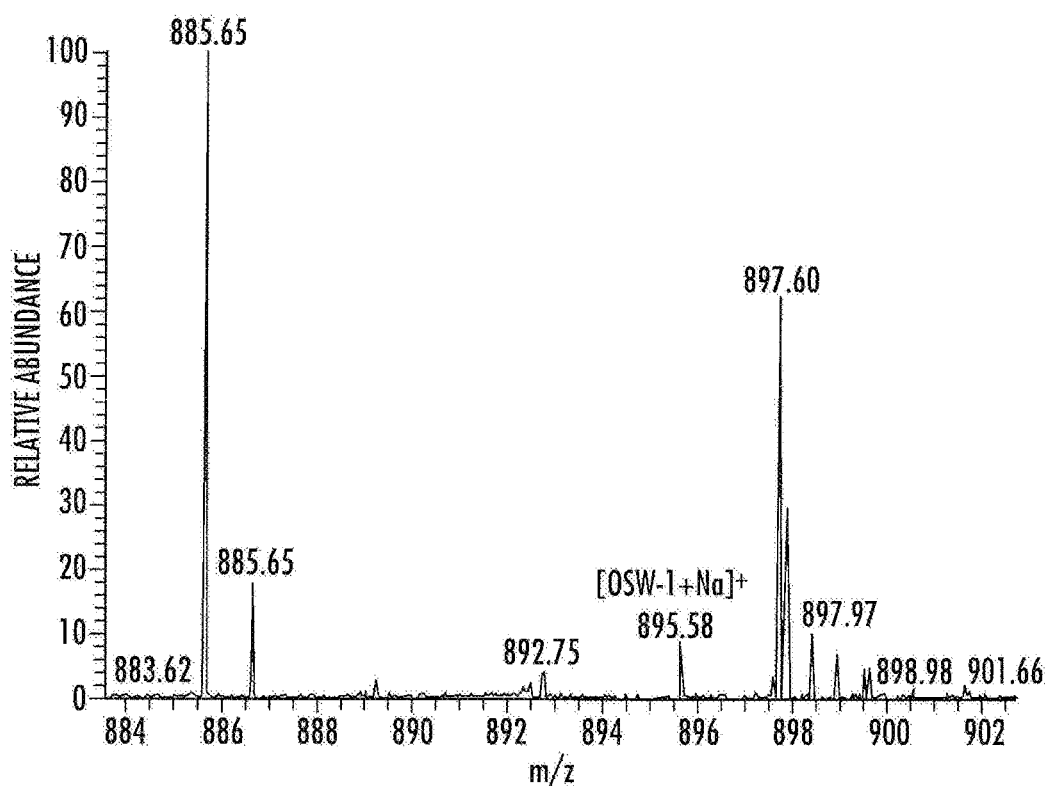
FIG. 11 depicts mass spectra obtained using a Single-probe inserted into a HeLa cell treated with OSW-1.

Similar to other high-resolution MSI newly described herein techniques, the Single-probe MSI can be used for single cell MS studies, in which the solvent droplet formed at the tip of the imaging probe can sample species inside of cells. Performing MS in living, single cells is potentially a major advancement in biological science, but only if it can be accomplished in situ in real-time, which other current techniques cannot achieve but is now achieved with the novel Single-probe described herein. Single-probe MS of single cells as enabled herein provides a novel way to understand the dynamic activities of the cell, particularly upon experimental stimuli. In fact, some cell lines critical for drug discovery studies, such as HeLa (cervical cancer) and NIH 3T3 (mouse embryonic kidney), are likely to be the best targets due to their relatively large size (>10 µm) and biological importance. In the presently disclosed inventive concepts, Single-probes having very sharp tips (e.g., having a tip diameter of 10 µm or less, e.g., see FIG. 9) can be fabricated. Such probe tip sizes are comparable in size to single cells. Experiments have been carried out on such cells using novel Single-probe devices such as disclosed herein. To demonstrate the ability of the Single-probe to measure and identify specific substances in a cell, HeLa cells were cultured and treated with OSW-1 (anti-cancer drug, 4 hours treatment). After being washed with PBS to remove OSW-1 present in the culture medium and absorbed on the cell surface, the cell-containing plate was placed under the Single-probe and a microscope (Supereyes T004 Electronic Digital Microscope). The Single-probe was inserted into cells by precisely lifting the z-translation stage (the minimum incremental motion of the stage is 0.1 µm), and the corresponding ion signals of OSW-1 species was monitored during the approach. Different spectra (FIG. 10) were observed while the imaging probe was still in the PBS (phosphate buffered saline) solution (before insertion into the cell), and after the probe was inserted into a single cell (FIG. 11). A significant change of the total ion intensities of OSW-1 species (m/z=895.58, sodium adduct ion) confirmed that OSW-1 was detected inside a single cell using the Single-probe MSI technique in situ and in real-time.

Example 6

The tips of the Single-probes of the presently disclosed inventive concepts can be formed to have extremely narrow diameters (e.g., as small as 0.03 µm). However, high electrical resistance, which is induced by extremely small inner diameters of channels inside of probe-tips and low electrical conductivity of solvent (i.e., methanol/water, acetonitrile), can hinder the sample ionization at the nanospray emitter end of the probe. For example, an ion signal can be difficult to observe when the tip size less than 8~9 µm, even though a smooth solvent flow can still be obtained from the primary capillary via a syringe, indicating that nanospray cannot be formed due to a significant voltage drop between the conductive union and nanospray emitter end of the probe. To overcome these obstacles, fabrication protocols of the imaging probe can be modified through three different approaches (FIGS. 12A-12F).

Figure 12A:
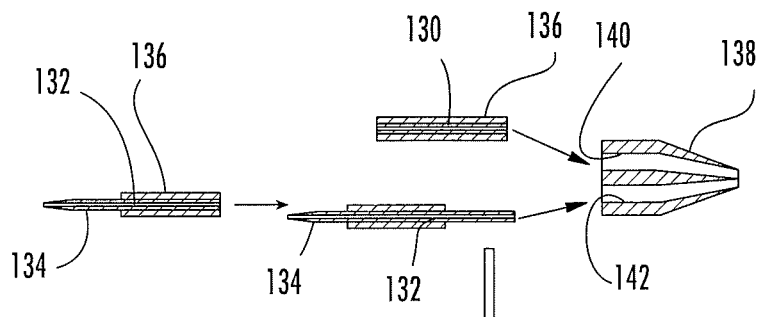
FIG. 12A-12F depicts capillaries and probes coated with Au (or other conductive material), 12A and 12B capillaries coated with a conductive material (e.g., gold) are inserted into a pulled dual-bore tube, 12C and 12D a pulled dual-bore tube is pulled then coated with a conductive material (e.g., gold) before insertion of the conductively-coated capillaries, 12E and 12F a Single-probe formed according to Example 3 is formed, then coated with a conductive material (e.g. gold).
Figure 12B:
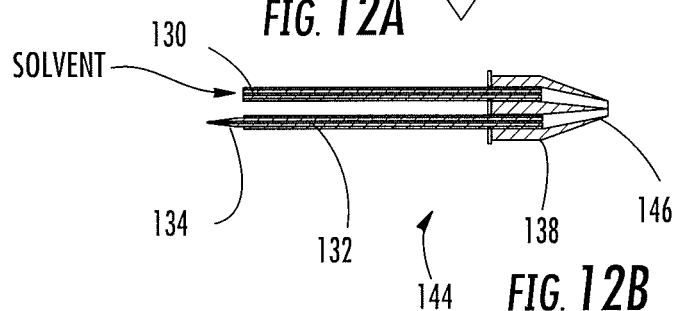

(a) Gold-coating nanospray emitters. The nanospray emitter capillaries inserted into the dual-bore quartz tube can be coated with gold or other conductive materials. Referring to FIGS. 12A and 12B, a pair of fused silica capillaries 130 and 132 having an outer coating material 136 are provided, as described herein in Examples 1-3. A tapered or sharp end 134 decoated of the outer coating material 136 of the capillary 132, used as the nanospray emitter, is coated with gold or other conductive materials. Additionally, a tube 138 having a first bore 140 and a second bore 142 is provided. The capillaries 130 and 132 are inserted into the first bore 140 and the second bore 142 of the tube 138, respectively, to form a probe 144 having a tip 146.

Figure 12C:
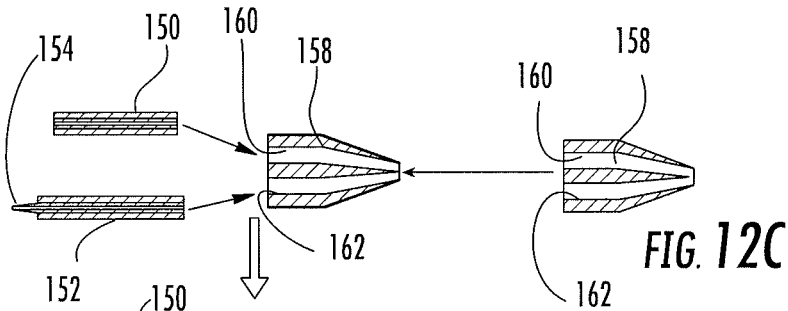
Figure 12D:
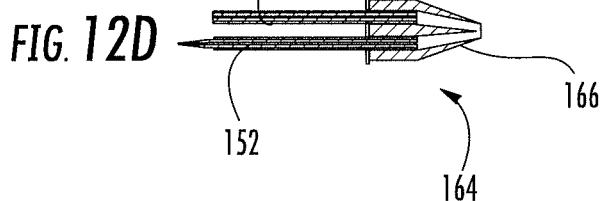

(b) Gold-coating pulled dual-bore quartz tubes. Referring to FIGS. 12C and 12D, a pair of fused silica capillaries 150 and 152 are provided, as described herein in Examples 1-3. Capillary 152 is provided with a tapered or sharp end 154 decoated of an outer coating material 156 of the capillary 152, used as the nanospray emitter. Additionally, a tube 158 having a first bore 160 and a second bore 162 is provided. The dual-bore quartz tube 158 which have been pulled (sharpened to a point) can be coated (e.g., by UHV Sputtering, Inc.) with gold or another conductive coating (e.g., coating having a thickness <1 µm). The capillaries 150 and 152 are inserted into the first bore 160 and the second bore 162 of the tube 158, respectively, to form a probe 164 having a tip 166. (FIGS. 12C and 12D).

Figure 12E:
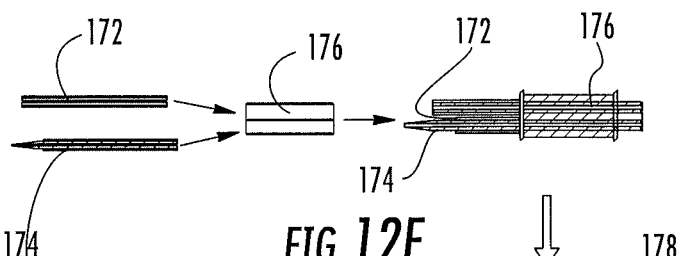
Figure 12F:
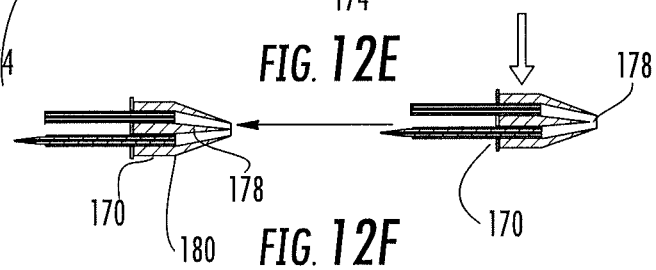
Figure 13:
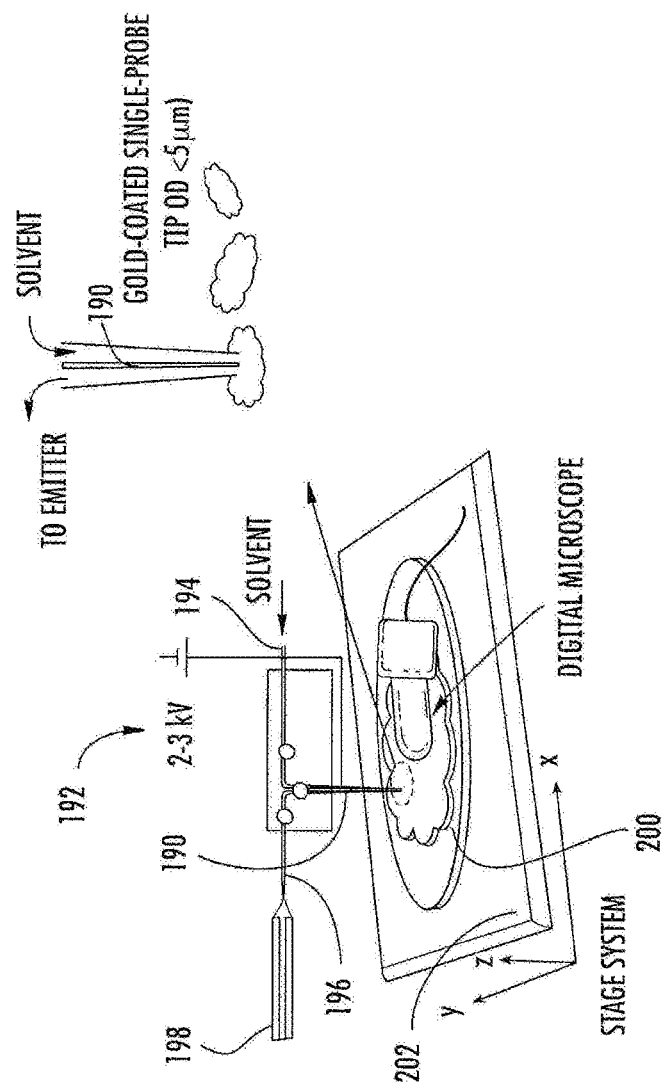
FIG. 13 depicts a non-limiting embodiment of a system of the present disclosure which uses a probe such as constructed in FIG. 12. An ionization potential is directly applied to the conductive coating on the low deadspace Single-probe.

(c) Gold-coating small dead-space Single-probes. Imaging probes fabricated through approaches a and b above may have a relatively large dead-space ("dead-volume") at the tip junction of the two capillaries. The effects of a dead-space become more pronounced in the case of analyzing a single cell. For example, the volume of a single cell (~10 µm diameter) is estimated to be only a few pico-liters. Referring to FIGS. 12E and 12F, to obtain a Single-probe 170 with a small volume dead space, fused silica capillaries 172 and 174 (with smaller ID) can be inserted through quartz dual-bore tubing 176, both ends glued, and pulled together using the laser puller. The capillaries and tubing will melt by laser heating and be simultaneously pulled forming a Single-probe 170 having low dead-space (low dead-volume) 178, which will be coated with gold or other conductive material 180 in a further step. Such coated probes produced from the methods described herein are coupled with a MSI device, and the ionization voltage can be directly applied to the gold coating (e.g., a low dead-space probe is represented in FIG. 13 as an example). Referring to FIG. 13, such a gold coated probe(s) 190 is shown utilized with a MS apparatus to provide a Single-probe MSI system 192. For example, the probe 190 having a first end 194 and a second end 196 can be attached to a support 198 (e.g., a glass slide) for example using epoxy or glue. The first end 194, which has a flat orifice, is used to provide a solvent. Voltage can be applied to the gold coating of the probe 190. The second end 196, which has a sharp emitter tip, is connected to an inlet 198 of the mass spectrometer (not shown) (e.g., Thermo LTQ Orbitrap XL mass spectrometer). The Single-probe MSI system 192 can be used to measure a tissue 200 on an X-Y-Z movable system 202.

Example 7

Using the present methods and probes, the actual abundance of a therapeutic molecule in a single cell can be determined. For example, the absolute abundance of deguelin inside single cells can be determined. For example, to measure OSW-1, a deuterated OSW-1 (OSW-1d) analog is used as an internal standard compound. The OSW-1d with known concentration is added into the solvent used to sample the analytes inside single cells. The OSW-1 present inside a cell is sampled and ionized, and its ion intensities are reported relative to the OSW-1d internal standard (e.g., normalization). The absolute abundance of OWS-1 is derived by integrating a set of results such as the relative ion intensities of OSW-1 and its deuterated form, the concentration of OSW-1d, the flow rate of international standard solution, and the MS accumulation time.

Example 8

As indicated above, when coupled with mass spectrometry (MS), the Single-probe of the presently disclosed inventive concepts can be used for the analysis of single eukaryotic cells and for the measurement of spatial distribution of chemicals on biological tissues. Additionally, the device can be used for the detection of proteins with posttranslational modifications (PTMs). Some of the most common post-translational modifications (PTMs) of proteins involve sulfation, phosphorelation, and/or carboxylation. Recently, the detection of the sulfated peptides has become an important topic in mass spectrometry (MS). Previous studies have been conducted using nano-electrospray ionization (nano-ESI) and desorption electrospray ionization (DESI) both with low pH sample solutions. However, the detection of sulfated peptides in the positive ion mode (common for proteomics studies) is hampered due to their rapid hydrolysis in solution.

Figure 14:
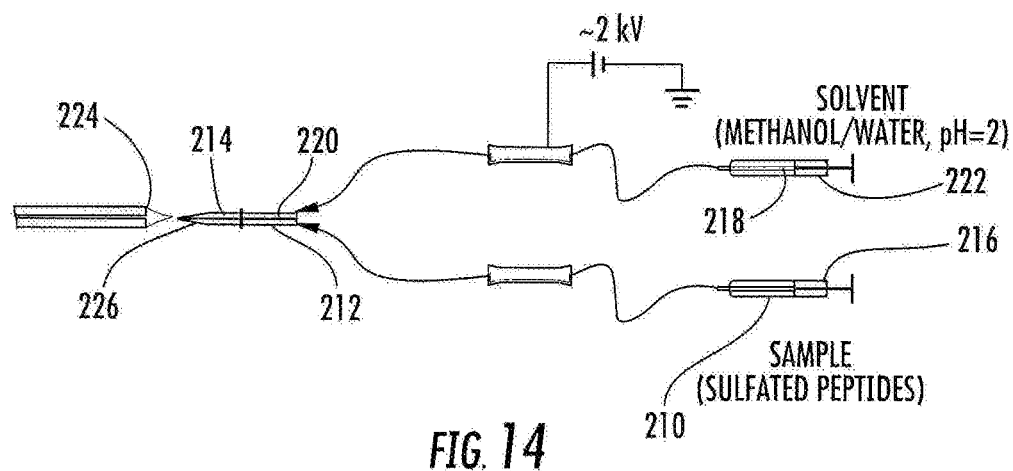
FIG. 14 depicts a system for detection of posttranslational modifications (PTMs).

Using the Single-probe MS technique of the present disclosure, as described herein, sulfated peptides and proteins can be detected. In one experiment for example, referring to FIG. 14, sulfated proteins are prepared in MeOH:H$_2$O solution 210, and infused into one capillary 212 of the Single-probe 214 using a syringe 216. Acidic MeOH:H$_2$O solution with pH=2 218 (using HCl) is infused into the other capillary 220 with a syringe 222 to enhance the ionization efficiency of proteins. The Single-probe 214 is placed towards the MS inlet 224 as explained elsewhere herein and the ionization potential (~2 kV) is applied. Two solutions are rapidly mixed at the probe tip 226, and the reaction time allowed for hydrolysis is significantly shortened; however, proteins are protonated due to the extremely fast reaction rate of protonation processes. Experimental results indicate that intact sulfated or phosphorylated protein ions were dominant, whereas the corresponding desulfation species was significantly reduced or completely eliminated.

Example 9

Use of the Single-Probe with a Micro-Funnel for Extracellular Compounds Analysis Above, a Single-probe device MS for analysis of compounds inside single cells is described. In fact, single cell level measurement of both intracellular and extracellular compounds has been a long-sought goal of biological and pharmaceutical studies. Especially, current single-cell MS developed techniques are unable to analyze living cells interacting with their surrounding normal environment and other cells. The MS analysis of small-molecular weight compounds excreted by mammalian cells, the lipid and metabolite components of the secretome, has not been extensively studied on the single cell level, due to the lack of analytical detection methods. The uncharted area of single cell non-protein secretome analysis holds a tremendous amount of promise.

Figure 15:
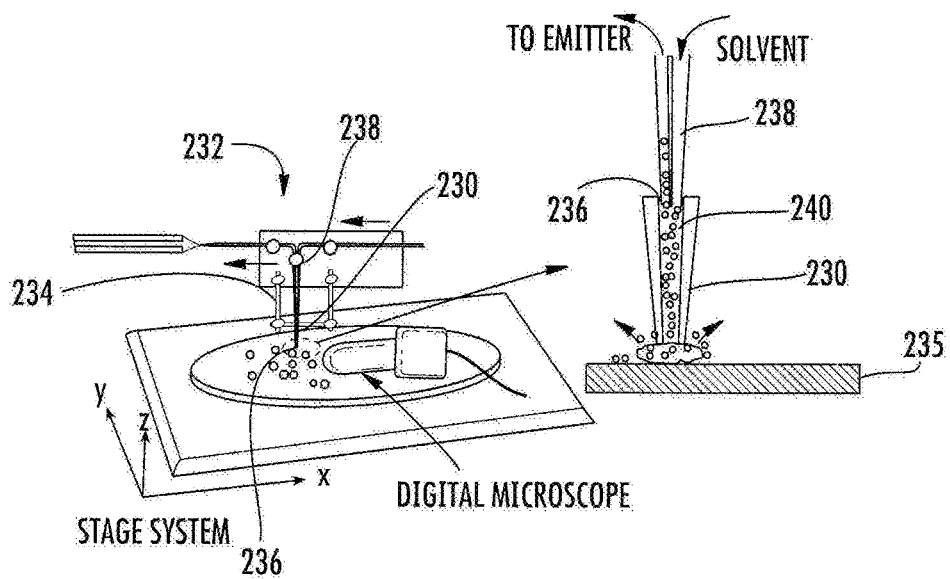
FIG. 15 depicts a probe and system which uses a "micro-funnel" in accordance with an embodiment disclosed herein.

In an alternative embodiment of the presently disclosed inventive concepts, a 'micro-funnel' adapter 230 for a Single-probe system 232 has been developed (FIG. 15). The Single-probe system 232 is similar to the Single-probe system(s) 192 (FIG. 13) except as described herein. The micro-funnel component 230 can be supported on a scaffold 234 that is built from thin fused silica capillary (e.g., 90 μm outer diameter). The scaffold 234 is thin enough to allow the micro-funnel component 230 to access a cell surface 235 while rigid enough to maintain stable structure during the sampling and MS measurement processes. The tip 236 of the Single-probe 238 is inserted into an upper orifice 240 of the micro-funnel component 230 to sample the chemical species inside the funnel 230. The micro-funnel 230 of the probe 238 is placed at the cell surface 235 to collect excreted molecules over the time (e.g. ~20 minutes) before MS analysis through the Single-probe 238. The Single-probe 238 is activated inside of the micro-funnel 230, to draw the solution there to the nano-ESI emitter via capillary action. The solvent used in the Single-probe 238 may be for example, either an aqueous buffer or an organic solvent, for example, that provides for better ionization efficiency. In one non-limiting embodiment the micro-funnel 230 is fabricated from a fused silica capillary pulled by laser puller. After pulling, it into a small piece (e.g., length: ~5 mm; upper opening OD: ~100 um, ID: 40 um; lower opening OD: 8-10 um, ID: ~5 um). The Single-probe tip 236 is inserted into the upper opening 240 of the micro-funnel 230. They can be held together through a scaffold 234 (e.g., made from fused silica capillaries). The internal volume of the micro-funnel 230 in this embodiment is in a range of from about 25 nL to about 200 nL, e.g., about 100 nL.

Example 10

In another embodiment, the present disclosure provides a new method to assess cellular targets of drug-candidate compounds using a newly devised nanoscale mass spectroscopic and protein separation technologies. With current experimental methods, it can be very difficult to identify the cellular target of a biologically-active small molecule. Inside of the cell, there are thousands of different proteins capable of interacting with a drug-candidate molecule, but only a tiny subset of all the cellular proteins are targeted by the biologically-active small molecule. This specific interaction between the small molecule and its protein target(s) triggers the cellular response leading to the observed biological activity of the small molecule. Without understanding how the drug-candidate compound triggers it biological-activity through binding its cellular target, therapeutic development for that compound cannot proceed.

Currently, the typical experimental approach to identifying the cellular target of a small molecule consists of affixing the compound to a solid resin, and then using this affinity resin to enrich for proteins that bind to the resin affinity chromatography). In order to affix the compound to the resin, this approach requires the ability to modify a position on the compound's structure without destroying its bioactivity. Additionally, this approach requires a relatively large amount of drug-candidate compound (e.g., >10 mg), and often this expensive, slow and labor-intensive experimental approach is not applicable nor successful for many compounds.

Figure 16:
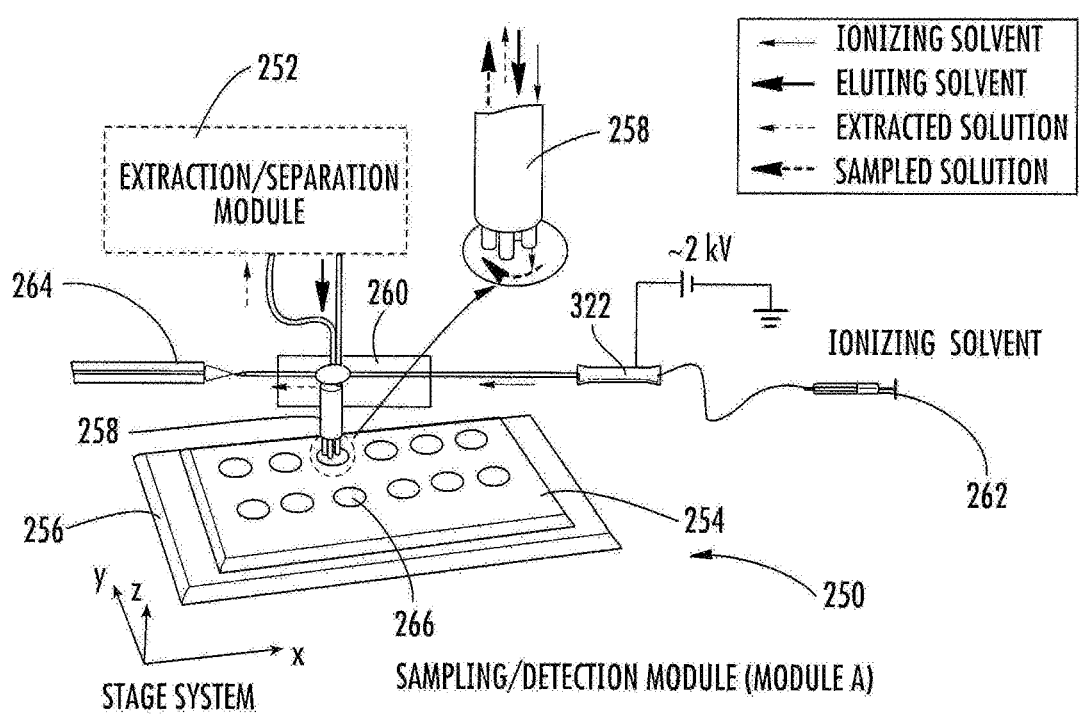
FIG. 16 depicts a system of the present disclosure using a sampling/detection module and an extraction/separation module utilizing a 4-bore probe.
Figure 17:
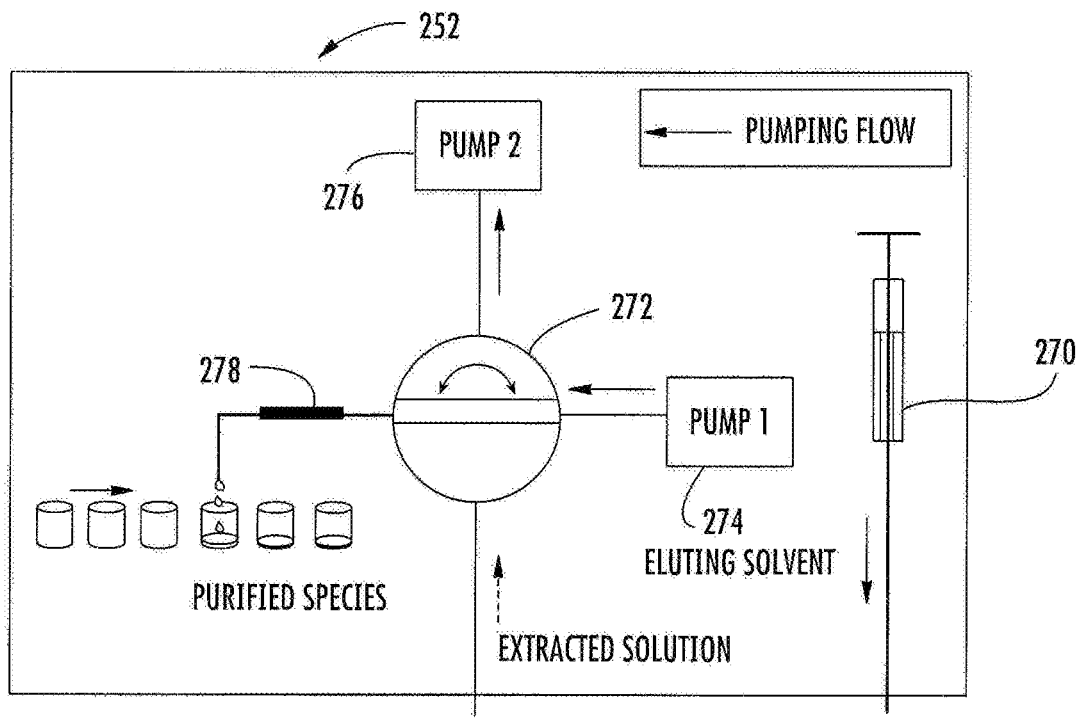
FIG. 17 depicts a micro-fabrication based capillary extraction/separation module used in FIG. 16.

In this embodiment of the presently described inventive concepts, a system for the rapid identification of a compound's cellular target without affinity-chromatography nor any chemical modification of the compound's structure is described. This system rapidly identifies the cellular target(s) using a miniscule amount of drug-candidate compound. The system is based on applying novel microscale bioseparation methods in conjunction with the newly proposed nanoscale mass spectrometric sampling and separation instrumentation described herein to identify the cellular targets of drug-candidate compounds. The system described herein includes two novel instrumentation/technology modules. Module A described herein is a mass spectrometry based sampling and detection device 250 (FIG. 16), and Module B is a micro-fabrication based capillary extraction and separation apparatus 252 (FIG. 17). In this system for example, a drug-candidate compound is mixed with a cellular lysate containing multiple (e.g., up to thousands) different proteins. This compound/lysate mixture is subjected to a microscale bioanalytical purification step to produce separate fractions that contain a limited number of proteins in each (e.g., about 10 proteins). The fractions are spotted as microdroplets on a surface, and then Module A and Module B are employed to (1) locate the drug-candidate compound in the multitude of microdroplets and (2) to identify the proteins that have co-purified with the compound, revealing putative cellular targets.

Referring to FIGS. 16-22, the mass spectrometry based sampling and detection device (Module A) 250 includes a multi-well sample feeder 254 mounted on a translational stage system 256, a multi-bore sampling and ionizing probe 258, a support 260, an ionizing solvent syringe 262 connected to an end of the probe 258 and a mass spectrometer inlet 264. The mass spectrometry based sampling and detection device (Module A) 250 is operationally connected to the micro-fabrication based capillary extraction and separation apparatus (Module B) 252. The micro-fabrication based capillary extraction and separation apparatus (Module B) 252 includes a syringe 270, an extraction pump device 272 having a first pump 274 and a second pump 276 and a separation column 278.

Major Components of Module A (a) Multi-well (vial) sample feeder. The drug-target containing solution is saved in the wells 266 on the plate or vials on the rack that are mounted on the translational stage system 256. The sample is fed by controlling 3 translational stages (x, y, and z directions) via a computer program.

Figure 18:
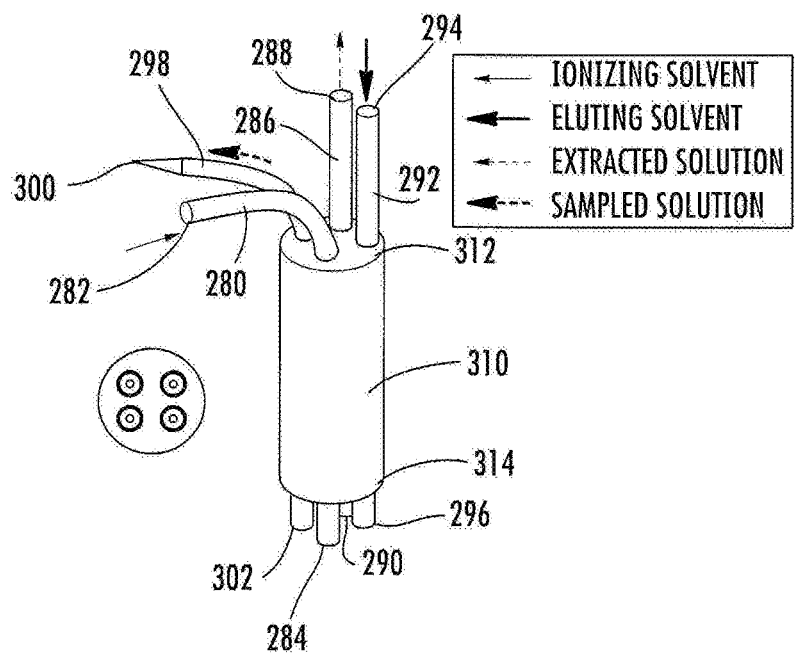
FIG. 18 depicts a non-limiting embodiment of a 4-bore sampling-ionizing probe used in the sampling/detection module of FIG. 16.
Figure 19:
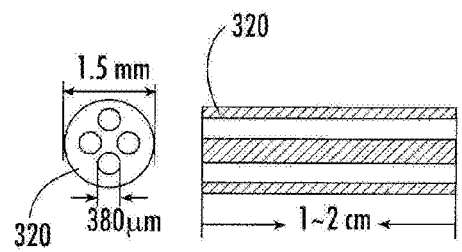
FIG. 19 depicts a 4-bore tube used in the fabrication of the 4-bore probe of FIG. 18.
Figure 20:
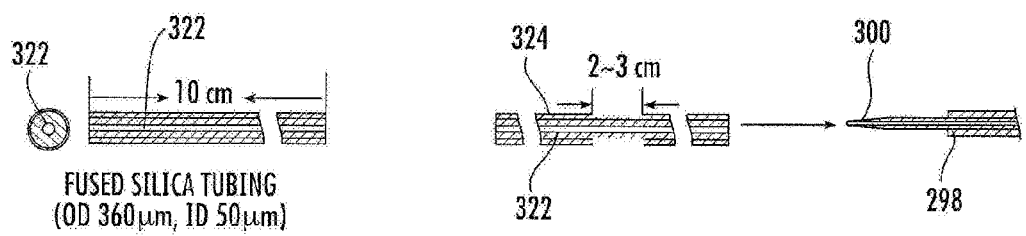
FIG. 20 depicts capillaries with portions of the coating removed therefrom for fabrication into emitter capillaries.
Figure 21:
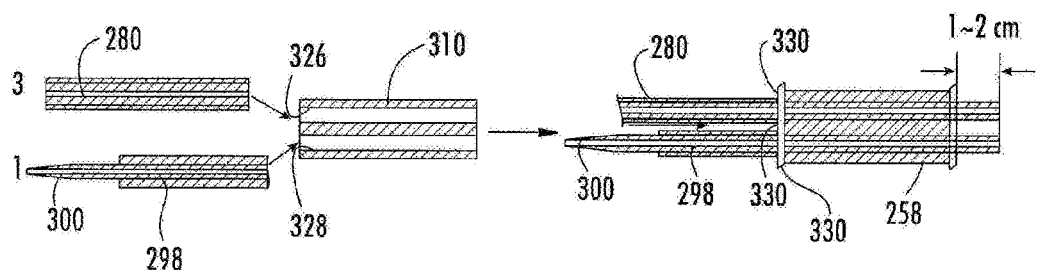
FIG. 21 depicts capillaries inserted into the 4-bore tube to form the 4-bore probe.

(b) Multi-bore sampling and ionizing probe. This novel probe 258 is fabricated by inserting 3 fused silica capillaries 280 having a first end 282 and a second end 284, 286 having a first end 288 and a second end 290 and 292 having a first end 294 and a second end 296 and 1 nano-ESI emitter (narrow tip) fused silica capillary 298 having a first end 300 and a second end 302 into a multi-bore glass tube 310 having a first end 312 and a second 314 (FIG. 18).

Working Mechanism of Module A

In one the experiment, the ionizing solvent (e.g., methanol/water solution) is supplied by one capillary 280, and mixed with sample solution (cell lysate) inside of wells 266 or vials. Due to the self-aspiration of liquid inside of capillary 280, the analyte of interest (e.g., drug-target complex) can be sucked to the nano-ESI emitter 286. An ionization voltage (~2 kV) is applied between the emitter 286 and the inlet of a mass spectrometer 264, and therefore the analytes are ionized here and analyzed by the mass spectrometer. The action of Module B 252 and the stage system 256 depend on the mass spectrometry results. A positive result, in which the species of interest are detected from the sample, will trigger Module B 252 and initiate the infusion of eluting solvent, the suction of analyte containing solution, and separation/collection of analyte. Once these processes are finished, the stage system 256 will move the next sample for analysis. In contrast, a negative result will only result in the motion of the stage system 256.

Fabrication of Module A (a) Multi-well (vial) sample feeder. The core component of this device is the stage system 256, including 3 independently controlled translational stages (for x, y, and z motion) and the controlling software. A similar system for mass spectrometry imaging measurement was established, in which the sample is mounted on a holder of the stage system 256. The sample position is controlled by the motion of these 3 translational stages under the command of a LabView program. The hardware of the current system can be directly used for the innovation, whereas a modification of control software can be made for the synchronized action of Modules A and B.

Figure 22:
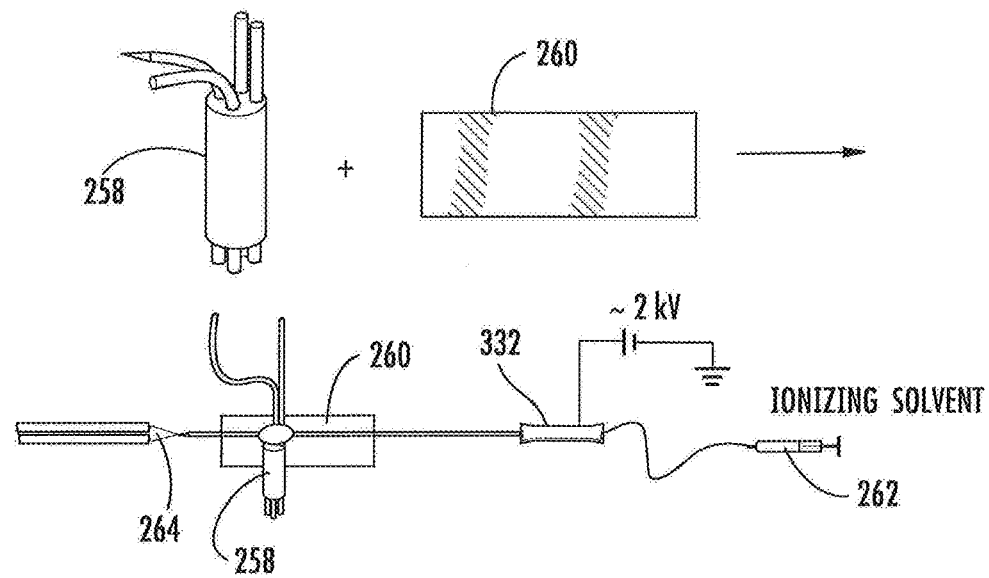
FIG. 22 depicts a non-limiting embodiment of the 4-bore probe implemented into an analysis system including an ionizing solvent.

(b) Multi-bore sampling and ionizing probe. The probe 258 is an integrated part for multiple functions. It enables the sampling of small amounts (e.g., <10 nL) of solution, ionization of the solution for mass spectrometry analysis, infusion of an eluting solvent into the solution, and extraction of the analyte containing solution for separation. Due to its small physical size (e.g., OD=1.5 mm) and low sampling volume, the probe 258 can be used to detect and extract species of interest from small amounts of samples. The multi-bore probe 258 can be directly exchanged with the dual-bore Single-probe described elsewhere herein, which is for the mass spectrometry imaging studies, to detect sample solution using mass spectrometer. One non-limiting embodiment of how the multi-bore Single-probe 258 can be fabricated is described as follows:

(1) Cut the multi-bore glass tube 320 (1.5 mm OD, 380 µm ID, Friedrich & Dimmock, Inc.) into 1~2 cm long pieces (FIG. 19), (2) Cut the fused silica capillary 322 (360 µm OD, 50 µm ID, PolyMicro Technologies) into 4 pieces (~10 cm long). Remove the coating material 324 (~3 cm long) in the middle of 1 tubing piece, and pull it into 2 pieces with a sharp tip one end 300 by using a laser puller (e.g., Sutter P-2000) to form the nano-ESI emitter (narrow tip) fused silica capillary 298 (FIG. 20), (3) Insert the blunt (flat) ends 284, 290, 296 and 302 of the 4 fused silica capillaries 280, 286, 292 and 298 (represented by 280 in FIG. 21) into the bores 326 and 328 of the 4-bore glass tube 310, and leave these ends 1-2 mm beyond one end 314 of the 4-bore tube 310. The narrow tip 300 of the nano-ESI emitter 298 and opposite blunt tips 282, 288 and 294 of the other three capillaries 280, 286 and 292 extend beyond the opposite end 312 of the 4-bore tube 310. Seal gaps 330 (e.g., using UV-light active epoxy-Prime Dent Light Cure Resin Dental Bonding Adhesive), and irradiate the whole piece with UV light for 30 seconds. The multi-bore sampling and ionizing probe 258 has been produced (FIG. 21), and (4) Integrate small parts into a unit probe device (FIG. 22). First, attach the multi-bore sampling and ionizing probe 258 to the support 260, e.g., a glass slide, using epoxy or glue. Second, make the connection between the probe 258 and the sampling/ionization circulation. Connect the blunt end of one fused silica capillary to the syringe 262 using the MicroTight Conductive Union 332 (Upchurch Scientific); the voltage can be applied to the union. Attach the other end 300, which has the sharp narrow emitter end, to the inlet 264 of the mass spectrometer. Third, make the connection between the probe 258 and the extraction/separation circulation 252. Connect the blunt end 294 of one fused silica capillary 292 to the syringe pump of Module B, which provides the eluting solvent. Connect the end 288 of the last fused silica capillary 286 to the extraction pumping device 272, which is connected with the separation column 278.

Example 11

Figure 23:
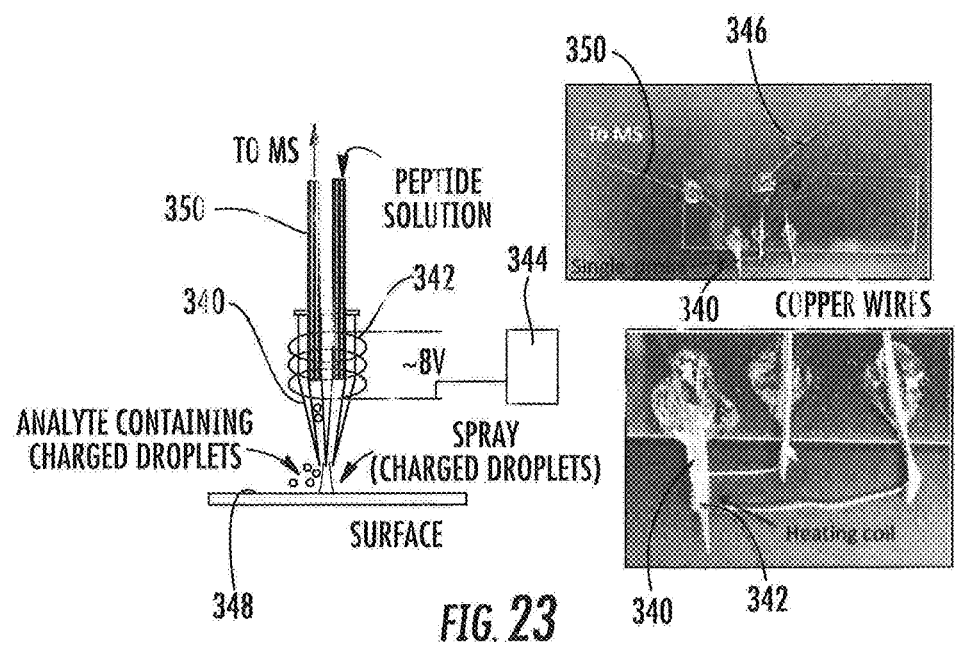
FIG. 23 depicts an alternate embodiment wherein a portion of the probe is heated.

In other embodiments of the presently disclosed inventive concepts, the probes comprise means for heating at least a portion of the probe. One non-limiting example of such a heated probe 340 is represented in FIG. 23, wherein a miniaturized heating coil 342 is wrapped around the Single-probe 340, and a power supplier 344 is used to apply a voltage (e.g., ~7-8 V) to the coil 342 (e.g., Cr—Ni filament, gauge 34). The solvent (e.g., methanol/water mixture), which is carried by a solvent providing capillary 346, is heated up and sprayed as charged droplets onto the surface of the sample 348. Analytes on the surface of the sample 348 are desorbed, ionized, and sucked into the other capillary 350, which is connected to an MS inlet (not shown), for MS analysis as described elsewhere herein.

The desorption and ionization mechanisms of the heated Single-probe MSI have some similarities to DESI (desorption electrospray ionization), a popular method for MS analysis of surfaces and tissue imaging. Advantages of the heated Single-probe MSI technique include less clogging (no surface contact and larger orifice), less carry-over from the previous measurement, and shorter time delay (no liquid but only gas flow in the nano-ESI emitter channel). Although heated Single-probe MSI has some similarities to DESI, heated Single-probe MSI provides a higher analyte resolution due to its small tip size (i.e., smaller sampling area).

Probes of the presently disclosed inventive concepts can be constructed with tubes having two or more bores, including dual-bore tubes, three-bore tubes, four-bore tubes, and other multi-bore tubes having for example 5, 6, 7, 8, 9, 10, or more separates bores. The ID of the bores of the tubes may be in a range of, but are not limited to, 1 μm to 500 μm, for example 5 μm to 400 μm, 10 μm to 300 μm, 20 μm to 200 μm, 5 μm to 200 μm, or any subrange of integers inclusive within the range 1 μm to 500 μm, such as 25 μm to 125 μm.

The capillaries used to make the probes (which are inserted into the tube bores) can have an ID in a range of, but not limited to, 1 μm to 150 μm, for example 5 μm to 150 μm, 10 μm to 100 μm, 20 μm to 750 μm, 25 μm to 50 μm, or any subrange of integers inclusive within the range 1 μm to 150 μm, such as 20 μm to 60 μm. The capillaries can have an OD in a range of, but not limited to, 5 μm to 450 μm, for example 10 μm to 350 μm, 20 μm to 300 μm, 40 μm to 250 μm, 50 μm to 200 μm, or any subrange of integers inclusive within the range 5 μm to 450 μm, such as 75 μm to 150 μm.

Once a tube has been pulled to form a tip of the probe, the tip can have an OD in a range of, but not limited to 0.03 μm to 50 μm, for example 0.1 μm to 50 μm, 0.5 μm to 30 μm, 1 μm to 25 μm, 1.5 μm to 20 μm, 2 μm to 15 μm, or any subrange of integers or fractions inclusive within the range 0.03 μm to 50 μm, including, but not limited to 1 μm, 1.5 μm, 2 μm, 2.5 μm, 3 μm, 3.5 μm, 4 μm, 4.5 μm, 5 μm, 5.5 μm, 6 μm, 6.5 μm, 7 μm, 7.5 μm, 8 μm, 8.5 μm, 9 μm, 9.5 μm, 10 μm, 10.5 μm, 11 μm, 11.5 μm, 12 μm, 12.5 μm, 13 μm, 13.5 μm, 14 μm, and 14.5 μm.

It will be understood from the foregoing description that various modifications and changes may be made in the various embodiments of the present disclosure without departing from their true spirit. For example, active regions and injection regions of the lasers can be constructed in a variety of manners and with various materials, and thicknesses of materials and layers. The description provided herein is intended for purposes of illustration only and is not intended to be construed in a limiting sense. Thus, while the presently disclosed inventive concepts have been described herein in connection with certain embodiments so that aspects thereof may be more fully understood and appreciated, it is not intended that the presently disclosed inventive concepts be limited to these particular embodiments. On the contrary, it is intended that all alternatives, modifications and equivalents are included within the scope of the presently disclosed inventive concepts as defined herein. Thus the examples described above, which include particular embodiments, will serve to illustrate the practice of the presently disclosed inventive concepts, it being understood that the particulars shown are by way of example and for purposes of illustrative discussion of particular embodiments of the presently disclosed inventive concepts only and are presented in the cause of providing what is believed to be a useful and readily understood description of procedures as well as of the principles and conceptual aspects of the inventive concepts. Changes may be made in the formulation of the various components and compositions described herein, the methods described herein or in the steps or the sequence of steps of the methods described herein without departing from the spirit and scope of the presently disclosed inventive concepts.

What is claimed is:

1. A sampling probe, comprising:
   a tube comprising at least a first bore, a second bore, a first end, and a tapered second end;
   a first capillary partially disposed within the first bore, at least a portion of the first capillary extending from the first end of the tube;
   a second capillary partially disposed within the second bore, the second capillary having a portion with a free end which extends from the first end of the tube;
   and wherein an end of the first bore and an end of the second bore converge to form a junction in the tapered second end of the tube, wherein the first bore of the tube is external to the second bore of the tube and the second bore is external to the first bore except at the junction.

2. The sampling probe of claim 1, further comprising at least a third capillary partially disposed within at least a third bore in the tube.

3. The sampling probe of claim 2, further comprising at least a fourth capillary partially disposed within at least a fourth bore in the tube.

4. The sampling probe of claim 1, wherein the tapered second end of the tube has an outer diameter in a range of 0.1 μm to 50 μm.

5. The sampling probe of claim 1, wherein the first bore and second bore of the tube have inner diameters in a range of 1 μm to 500 μm.

6. The sampling probe of claim 1, wherein the first capillary and second capillary have inner diameters in a range of 1 μm to 150 μm.

7. The sampling probe of claim 1, wherein the first capillary and second capillary have outer diameters in a range of 5 μm to 450 μm.

8. The sampling probe of claim 1, further comprising: a heating element positioned about at least a portion of the tube.

9. A sample analysis system comprising the sampling probe of claim 1 in fluid communication with a mass spectrometer via the free end of the second capillary, and in fluid communication with a solvent source via the first capillary.

10. The sample analysis system of claim 9, further comprising a microfunnel into which the tapered second end of the sampling probe is disposed.

11. A method of sampling a cell or tissue source, comprising: obtaining a sample from the cell or tissue source via a sample analysis system comprising the sampling probe of claim 1 which is in fluid communication with (1) a mass spectrometer via the free end of the second capillary, and (2) a solvent source via the first capillary, the method comprising providing a solvent to the cell or tissue sample via the first capillary and extracting the sample via the second capillary and transferring the sample to the mass spectrometer for analysis.

* * * * *